United States Patent
Yanagi et al.

(10) Patent No.: US 10,925,861 B2
(45) Date of Patent: Feb. 23, 2021

(54) MIRABEGRON-CONTAINING TABLET, METHOD FOR PRODUCING MIRABEGRON-CONTAINING PHARMACEUTICAL PREPARATION, AND METHOD FOR PRODUCING MIRABEGRON-CONTAINING GRANULATED PRODUCT

(71) Applicant: SAWAI PHARMACEUTICAL CO., LTD., Osaka (JP)

(72) Inventors: Toshihiro Yanagi, Osaka (JP); Kenji Nozawa, Osaka (JP); Kaori Umemura, Osaka (JP); Masatoshi Arimura, Osaka (JP); Akiko Takada, Osaka (JP)

(73) Assignee: SAWAI PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 15/908,599

(22) Filed: Feb. 28, 2018

(65) Prior Publication Data

US 2018/0185339 A1 Jul. 5, 2018

Related U.S. Application Data (63) Continuation of application No. PCT/JP2016/071140, filed on Jul. 19, 2016.

(30) Foreign Application Priority Data

Sep. 1, 2015 (JP) .............................. JP2015-171666

(51) Int. Cl.
| | |
|---|---|
| *A61K 31/426* | (2006.01) |
| *A61K 9/16* | (2006.01) |
| *A61K 9/20* | (2006.01) |
| *A61K 47/32* | (2006.01) |
| *A61K 47/38* | (2006.01) |

(52) U.S. Cl.
CPC .......... *A61K 31/426* (2013.01); *A61K 9/1635* (2013.01); *A61K 9/1652* (2013.01); *A61K 9/1694* (2013.01); *A61K 9/2027* (2013.01); *A61K 9/2054* (2013.01); *A61K 9/2095* (2013.01); *A61K 47/32* (2013.01); *A61K 47/38* (2013.01)

(58) Field of Classification Search
CPC ...... A61K 31/426; A61K 47/32; A61K 47/38; A61K 9/1635; A61K 9/1652; A61K 9/1694; A61K 9/2027; A61K 9/2054; A61K 9/2095; A61P 13/10
See application file for complete search history.

(56) References Cited

U.S. PATENT DOCUMENTS

| | | | |
|---|---|---|---|
| 2006/0115540 A1 | 6/2006 | Takasu et al. | |
| 2008/0096924 A1 | 4/2008 | Masuda et al. | |
| 2010/0144807 A1 | 6/2010 | Takaishi et al. | |
| 2012/0070465 A1 | 3/2012 | Takaishi et al. | |
| 2013/0137739 A1 | 5/2013 | Sakurai et al. | |
| 2015/0031734 A1* | 1/2015 | Kasashima | .......... A61K 31/426 514/370 |

FOREIGN PATENT DOCUMENTS

| | | |
|---|---|---|
| CN | 104288117 A | 1/2015 |
| EP | 1413294 B1 | 9/2010 |
| JP | 4688089 B2 | 5/2011 |
| JP | 2014-507449 A | 3/2014 |
| JP | 2015-515522 A | 5/2015 |
| JP | 2016-188181 A | 11/2016 |
| WO | 2004041276 A1 | 5/2004 |
| WO | 2006064906 A1 | 6/2006 |
| WO | 2010038690 A1 | 4/2010 |
| WO | 2011152297 A1 | 8/2011 |
| WO | 2011/122524 A1 | 10/2011 |
| WO | 2012119841 A1 | 9/2012 |
| WO | 2012156998 A2 | 11/2012 |
| WO | 2013154981 A1 | 10/2013 |

OTHER PUBLICATIONS

Written Opinion of the International Searching Authority for PCT/JP2016/071140 dated Aug. 30, 2016.
Kalariya, P.D. et al., Characterization of stress degradation products of mirabegron using UPLC-QTOF-MS/MS and in silico toxicity predictions of its degradation products, RSC Advances, Mar. 26, 2015, vol. 5, p. 31024-31038, Royal Society of Chemistry.
The International Search Report for PCT/JP2016/071140 dated Aug. 30, 2016, citing the above references.
English Translation of Written Opinion of the International Searching Authority of corresponding international application PCT/JP2016/071140.
Extended European search report for the counterpart European Patent application No. 16841313.6 dated Mar. 13, 2019, citing above reference.
Japanese Office Action dated Jul. 2, 2019 for corresponding Japanese Application No. 2015-171666, citing the above references with partial English Machine Translation.

(Continued)

*Primary Examiner* — Sahar Javanmard
(74) *Attorney, Agent, or Firm* — Hauptman Ham, LLP (57) ABSTRACT

To provide a mirabegron-containing tablet that maintains the amorphous form of mirabegron even after long-term storage. Also, to provide a mirabegron-containing pharmaceutical preparation that can maintain the purity of mirabegron while preventing the generation of related substances at the time of storage, a method for producing a mirabegron-containing pharmaceutical preparation, and a method for producing a mirabegron-containing granulated product. According to an embodiment of the present invention, there is provided a mirabegron-containing pharmaceutical preparation containing mirabegron, hypromellose, and polyvinylpyrrolidone. The mirabegron-containing pharmaceutical preparation may contain a spray-dried granulated product containing the mirabegron, the hypromellose, and the polyvinylpyrrolidone.

6 Claims, 4 Drawing Sheets

(56) References Cited

OTHER PUBLICATIONS

Communication pursuant to Article 94(3) EPC issued for corresponding European Patent Application No. 16 841 313.6 dated Sep. 9, 2020.
Arpagaus et al., "Scale-up from bench-top research to laboratory production", Buchi Information Bulletin, vol. 52, 2008, pp. 1-8, cited in NPL No. 1.
Ré, "Formulating Drug Delivery Systems by Spray Drying", Drying Technology, vol. 24, No. 4, 2006, pp. 443-446, cited in NPL No. 1.
Jain et al., "Formulation and Evaluation of Spray-Dried Esomeprazole Magnesium Microspheres", Tropical Journal of Pharmaceutical Research, vol. 12, No. 3, Jun. 2013, pp. 299-304, cited in NPL No. 1.

* cited by examiner

FIG. 1

| | Example 1 | Example 2 | Example 3 | Comparative example 1 | Comparative example 2 | Comparative example 3 | Comparative example 4 | Comparative example 5 | Comparative example 6 | Comparative example 7 | Comparative example 8 | Comparative example 9 |
|---|---|---|---|---|---|---|---|---|---|---|---|---|
| | HPMC 50% PVP 50% | HPMC 62.5% PVP 62.5% | HPMC 75% PVP 75% | MC 100% | HPMC 50% | HPMC 100% | HPMC 125% | HPMC 150% | PVP 50% | PVP 100% | PVP 125% | PVP 150% |
| 2 weeks | amorphous | amorphous | amorphous | amorphous | α-type crystal | amorphous | amorphous | | amorphous | amorphous | amorphous | amorphous |
| 4 weeks | amorphous | amorphous | amorphous | α-type crystal | α-type crystal | α-type crystal | α-type crystal | α-type crystal | amorphous | amorphous | amorphous | amorphous |
| 2 months | amorphous | amorphous | amorphous | α-type crystal | α-type crystal | α-type crystal | α-type crystal | α-type crystal | α-type crystal | α-type crystal | amorphous | amorphous |
| 3 months | amorphous | amorphous | amorphous | α-type crystal | α-type crystal | α-type crystal | α-type crystal | α-type crystal | α-type crystal | α-type crystal | amorphous | amorphous |
| 6 months | amorphous | amorphous | amorphous | α-type crystal | α-type crystal | α-type crystal | α-type crystal | α-type crystal | α-type crystal | α-type crystal | amorphous | amorphous |

FIG. 2

| | Example 1<br>HPMC 50%<br>PVP 50% | Example 1<br>HPMC 62.5%<br>PVP 62.5% | Example 1<br>HPMC 75%<br>PVP 75% | Comparative example 1<br>MC 100% | Comparative example 2<br>HPMC 50% | Comparative example 3<br>HPMC 100% | Comparative example 4<br>HPMC 125% | Comparative example 5<br>HPMC 150% | Comparative example 6<br>PVP 50% | Comparative example 7<br>PVP 100% | Comparative example 8<br>PVP 125% | Comparative example 9<br>PVP 150% |
|---|---|---|---|---|---|---|---|---|---|---|---|---|
| Initial | 0.26 | 0.38 | 0.26 | 0.18 | 0.18 | 0.24 | 0.29 | 0.19 | 0.24 | 0.29 | 0.34 | 0.47 |
| 2 weeks | 0.59 | 0.77 | 0.69 | 0.49 | | 0.58 | 0.56 | 0.45 | 0.67 | 0.82 | 1.05 | 1.28 |
| 4 weeks | 0.81 | 0.90 | 0.96 | 0.59 | | | | | 0.94 | 1.07 | 1.77 | 1.63 |
| 2 months | 1.82 | 1.45 | 2.06 | | | | | | | | 2.91 | 3.32 |
| 3 months | 2.43 | 2.07 | 2.97 | | | | | | | | 4.09 | 4.53 |
| 6 months | 5.49 | 4.30 | 5.28 | | | | | | | | 7.88 | 7.56 |

FIG. 3

| | Example 4 | Example 5 | Example 6 |
|---|---|---|---|
| (HPMC+PVP+PEG)/PEO | 80/20 | 73/27 | 67/33 |
| 2 weeks | amorphous | amorphous | amorphous |
| 4 weeks | amorphous | amorphous | amorphous |
| 2 months | amorphous | amorphous | amorphous |
| 3 months | amorphous | amorphous | amorphous |
| 6 months | amorphous | amorphous | amorphous |

MIRABEGRON-CONTAINING TABLET, METHOD FOR PRODUCING MIRABEGRON-CONTAINING PHARMACEUTICAL PREPARATION, AND METHOD FOR PRODUCING MIRABEGRON-CONTAINING GRANULATED PRODUCT

CROSS REFERENCE TO RELATED APPLICATIONS

This application is based upon and claims the benefit of priority from the prior Japanese Patent Application No. 2015-171666, filed on Sep. 1, 2015, and PCT Application No. PCT/JP2016/071140, filed on Jul. 19, 2016, the entire contents of which are incorporated herein by reference.

FIELD

The present invention relates to a mirabegron-containing pharmaceutical preparation, a method for producing a mirabegron-containing pharmaceutical preparation, and a method for producing a mirabegron-containing granulated product. In particular, the present invention relates to a stable mirabegron-containing tablet that can maintain the amorphous form of mirabegron after long-term storage, a method for producing a mirabegron-containing pharmaceutical preparation, and a method for producing a mirabegron-containing granulated product.

BACKGROUND

Mirabegron (2-(2-Amino-1, 3-thiazol-4-yl)-N-[4-(2-[[(2R)-2-hydroxy-2-phenylethyl]amino]ethyl)phenyl]acetamide) is a medical agent that has a selective $β_3$ receptor stimulating effect and is effective for a medical treatment for the overactive bladder.

For example, International Publication No. WO2004/041276 discloses a therapeutic substance for the overactive bladder, which contains, as an active component, (R)-2-(2-Aminothiazol-4-yl)-4'-[2-[(2-hydroxy-2-phenylethyl) amino]ethyl]acetic acid anilide or its salt.

Japanese Patent No. 4688089 discloses a controlled-release pharmaceutical composition for oral administration, which contains (1) (R)-2-(2-aminothiazol-4-yl)-4'-[2-[(2-hydroxy-2-phenylethyl)amino]ethyl]acetic acid anilide or its pharmaceutically acceptable salt, (2) at least polyethylene glycol as an additive that ensures penetration of water into a pharmaceutical preparation having a solubility in water such that the volume of water required for dissolving 1 g of the additive is 10 mL or less, and (3) a polyethylene oxide as a hydrogel-forming polymer having at least an average molecular weight of 1,000,000 or more and 2,000,000 or less, or a viscosity of 400 mPa·s or more and 4,000 mPa·s or less at a 2% aqueous solution at 25° C.

Mirabegron is a hardly soluble compound that has a poor solubility in water. For this reason, in order to obtain good bioavailability, it is necessary to improve the solubility of mirabegron. In general, a drug in an amorphous form is more soluble in water than in a crystal form. There is therefore a possibility that the bioavailability of mirabegron can be improved by maintaining mirabegron in an amorphous form in a pharmaceutical preparation. Accordingly, demands have arisen for a mirabegron-containing pharmaceutical preparation that can maintain mirabegron in an amorphous form not only immediately after production but also after long-term storage. In addition, demands have arisen for a mirabegron-containing pharmaceutical preparation that can maintain the purity of mirabegron while preventing the generation of related substances at the time of storage. However, no studies have been made about the amorphization of mirabegron and the maintenance of mirabegron in an amorphous form in long-term storage in such a mirabegron-containing pharmaceutical preparation.

SUMMARY

The present invention has studied for the first time the amorphization of mirabegron and the maintenance of mirabegron in an amorphous form after long-term storage in such a mirabegron-containing pharmaceutical preparation, which have not been studied so far. The present invention has an object to provide a mirabegron-containing tablet that maintains the amorphous form of mirabegron even after long-term storage. The present invention has another object to provide a mirabegron-containing pharmaceutical preparation that can maintain the purity of mirabegron while preventing the generation of related substances at the time of storage, a method for producing a mirabegron-containing pharmaceutical preparation, and a method for producing a mirabegron-containing granulated product.

According to an embodiment of the present invention, there is provided a mirabegron-containing pharmaceutical preparation characterized by containing mirabegron, hypromellose, and polyvinylpyrrolidone.

The mirabegron-containing pharmaceutical preparation may contain a spray-dried granulated product containing the mirabegron, the hypromellose, and the polyvinylpyrrolidone.

In the mirabegron-containing pharmaceutical preparation, the spray-dried granulated product may contain 100% or more by mass of the hypromellose and the polyvinylpyrrolidone in total with respect to a content of the mirabegron.

According to an embodiment of the present invention, there is provided a method for producing a mirabegron-containing pharmaceutical preparation, characterized by comprising dissolving mirabegron, hypromellose, and polyvinylpyrrolidone in a solvent, spray-drying and granulating a solution containing the mirabegron, the hypromellose, and the polyvinylpyrrolidone to obtain a granulated product containing amorphous mirabegron, granulating the granulated product with various types of pharmaceutically acceptable additives by using a wet granulation method, and tableting a mixed powder containing the obtained granulated particles to produce a tablet.

In the method for producing a mirabegron-containing pharmaceutical preparation, the solution may contain 100% or more by mass of the hypromellose and the polyvinylpyrrolidone in total with respect to a content of the mirabegron.

According to an embodiment of the present invention, there is provided a method for producing a mirabegron-containing granulated product, characterized by comprising dissolving mirabegron, hypromellose, and polyvinylpyrrolidone in a solvent, and spray-drying and granulating a solution containing the mirabegron, the hypromellose, and the polyvinylpyrrolidone.

In the method for producing a mirabegron-containing granulated product, the solution may contain 100% or more by mass of the hypromellose and the polyvinylpyrrolidone in total with respect to a content of the mirabegron.

DESCRIPTION OF EMBODIMENTS

Mirabegron-containing pharmaceutical preparations according to the present invention will be described below. Note, however, that the interpretation of the mirabegron-containing pharmaceutical preparations according to the present invention is not limited by the written contents of the following embodiment and examples. Note that in the present invention, "internal addition" indicates addition and mixing when a granulated product containing amorphous mirabegron is obtained by granulation with other additives using a fluid bed. In addition, in the present invention, "post-addition" indicates addition and mixing after particles containing an active component are granulated, dried, and sized.

The present inventors have newly found that the amorphous form of a mirabegron-containing pharmaceutical preparation after long-term storage can be maintained by preparing a granulated product containing mirabegron, hypromellose, and polyvinylpyrrolidone and tableting the product together with other additives. The present inventors have recognized that although hypromellose and polyvinylpyrrolidone each have the effect of maintaining the amorphous form of mirabegron, the addition of only polyvinylpyrrolidone maintains the amorphous form of mirabegron but exhibits a tendency to increase related substances when the product is stored under accelerated conditions. In contrast to this, the present inventors have confirmed that the addition of only hypromellose prevents the generation of related substances but makes mirabegron become easily crystallized.

The present invention has found for the first time that combining the complementary actions of hypromellose and polyvinylpyrrolidone can maintain the amorphous form of mirabegron in a mirabegron-containing pharmaceutical preparation after long-term storage and prevent the generation of related substances.

A mirabegron-containing pharmaceutical preparation according to the present invention is characterized by containing a spray-dried granulated product containing mirabegron, hypromellose, and polyvinylpyrrolidone. Hypromellose and polyvinylpyrrolidone are added in a mirabegron-dissolved solvent. Spray-drying the resultant product will amorphize the mirabegron and maintain the amorphous form of the mirabegron in the mirabegron-containing pharmaceutical preparation even after long-term storage. A mirabegron-containing pharmaceutical preparation according to the present invention is a pharmaceutical preparation obtained by preparing a granulated product containing mirabegron, hypromellose, and polyvinylpyrrolidone, mixing the granulated product with various types of additives, performing wet granulation using a solvent containing a binder, and tableting the mixed powder obtained through a drying process and sizing process.

According to an embodiment, a spray-dried granulated product containing mirabegron can maintain the amorphous form of the mirabegron in a mirabegron-containing pharmaceutical preparation after long-term storage by containing 100% or more by mass of hypromellose and polyvinylpyrrolidone in total with respect to the content of the mirabegron.

As described above, although hypromellose and polyvinylpyrrolidone each have the effect of maintaining the amorphous form of mirabegron, the addition of only polyvinylpyrrolidone maintains the amorphous form of mirabegron but generates related substances when the product is stored under accelerated conditions. In contrast to this, the addition of only hypromellose prevents the generation of related substances but makes mirabegron become easily crystallized. For this reason, hypromellose and polyvinylpyrrolidone are added in a spray-dried granulated product containing mirabegron at a ratio which complementary effects can be obtained. For example, hypromellose and polyvinylpyrrolidone can be added in a spray-dried granulated product containing mirabegron at a ratio of 1:1. However, the present invention is not limited to this.

A mirabegron-containing pharmaceutical preparation according to the present invention may contain 25 mg or 50 mg of mirabegron per tablet. However, this is not exhaustive.

A mirabegron-containing pharmaceutical preparation according to the present invention can use various types of additives upon internal addition and post-addition, and may further contain a lubricant or the like.

Mirabegron has a selective $\beta_3$ receptor stimulating effect, and hence is preferably made into a sustained-release pharmaceutical preparation, with the dissolution performance of mirabegron from the pharmaceutical preparation being controlled to prevent mirabegron from being rapidly absorbed into the body upon administration of the pharmaceutical preparation. As an additive for providing a sustained-release effect to the mirabegron-containing pharmaceutical preparation according to the present invention, it is possible to use, for example, a combination of polyethylene glycol and polyethylene oxide. Polyethylene glycol has a structure similar to that of polyethylene oxide, but is lower in molecular weight than polyethylene oxide and has the property of being easily dissolved in water. Accordingly, using a combination of polyethylene glycol and polyethylene oxide can effectively control the dissolution performance of mirabegron.

According to the present invention, each hypromellose and polyvinylpyrrolidone added in a mirabegron-dissolved solvent is a water-soluble polymer and expected to have a sustained-release function. In a mirabegron-containing pharmaceutical preparation according to the present invention, therefore, the dissolution performance of the mirabegron can be controlled by adjusting the ratio between the additive amount of hypromellose (HPMC), polyvinylpyrrolidone (PVP), and polyethylene glycol (PEG) and the additive amount of polyethylene oxide (PEO). The additive amount ratio (HPMC+PVP+PEG)/PEO can be determined based on the desired dissolution behavior of mirabegron, and is not specifically limited.

Lubricants to be used include, for example, metallic stearate, sucrose fatty acid ester, talc, light anhydrous silicic acid, aqueous silicon dioxide, and hardened oil, and preferably include metallic stearate and preferably include magnesium stearate.

A mirabegron-containing pharmaceutical preparation according to the present invention may also contain dibutylhydroxytoluene (BHT) as an antioxidant.

(Production Method)

A mirabegron-containing pharmaceutical preparation according to the present invention can be produced by a production method known in a pharmaceutical field. In order to amorphize mirabegron, it is preferable to obtain a granulated product containing mirabegron by using a spray-dried granulated product. For example, mirabegron, hypromellose, and polyvinylpyrrolidone are dissolved in a solvent, and the solution containing mirabegron, hypromellose, and polyvinylpyrrolidone is spray-dried and granulated. The obtained granulated product and other additives are mixed and screened, and the resultant product is wet-granulated using a solution containing a binder, thereby obtaining a sized granulated product through a drying process and a sizing process. A powder containing mirabegron before tableting can be obtained by mixing the obtained sized granulated product with a lubricant. A mirabegron-containing pharmaceutical preparation according to the present invention can be produced by tableting the powder containing mirabegron before tableting.

As a solvent in which mirabegron, hypromellose, and polyvinylpyrrolidone are dissolved, for example, a mixed solvent of dichloromethane and ethanol can be used. However, this is not exhaustive. In addition, the production method according to the present invention can use a commercially available spray-drying granulation apparatus. Note that tableting can be performed by a usual method using a commercially available tableting machine.

In a method for producing a mirabegron-containing pharmaceutical preparation according to the present invention, hypromellose and polyvinylpyrrolidone are added when a spray-dried granulated product containing mirabegron is prepared. It is preferable to add 100% or more by mass of hypromellose and polyvinylpyrrolidone in total with respect to 100% by mass of mirabegron. In the method for producing a mirabegron-containing pharmaceutical preparation according to the present invention, mirabegron is amorphized and the amorphous form of the mirabegron in the mirabegron-containing pharmaceutical preparation is maintained even after long-term storage by adding hypromellose and polyvinylpyrrolidone in the product, when a spray-dried granulated product containing mirabegron is prepared.

Hypromellose and polyvinylpyrrolidone are added in a spray-dried granulated product containing mirabegron at a ratio which complementary effects can be obtained for the maintenance of the amorphous form of the mirabegron. For example, hypromellose and polyvinylpyrrolidone can be added into the spray-dried granulated product containing the mirabegron at a ratio of 1:1.

As described above, in the method for producing the mirabegron-containing pharmaceutical preparation according to the present invention, it is possible to perform wet granulation for an amorphous spray-dried granulated product containing mirabegron together with a combination of polyethylene glycol and polyethylene oxide as additives having sustained-release performance. The additive amount ratio (HPMC+PVP+PEG)/PEO can be determined based on the desired dissolution behavior of mirabegron.

(Verification of Amorphization)

It is possible to check by a powder X-ray diffraction method whether mirabegron in a mirabegron-containing pharmaceutical preparation according to the present invention is amorphous. In a mirabegron-containing pharmaceutical preparation, an α-type crystal is mainly detected, and hence the presence/absence of a crystal can be checked based on whether an α-type crystal diffraction peak is detected.

(Dissolution Test)

Assume that in this specification, the dissolution rate of mirabegron is evaluated by measuring the dissolution rate of mirabegron in a tablet using USP Apparatus 1 (rotating basket method). Assume that a dissolution test uses a pH 6.8 USP buffer.

EXAMPLES

The above mirabegron-containing pharmaceutical preparation according to the present invention will be described in more detail by following examples and test results.

Example 1

In Example 1, hypromellose and polyvinylpyrrolidone were added by 100% by mass in total with respect to 100% by mass of mirabegron. Note that hypromellose and polyvinylpyrrolidone were added at a ratio of 1:1. Mirabegron of 20.0 g, 10.0 g of hypromellose (Shin-Etsu Chemical Co., Ltd., grade: TC-5E), and 10.0 g of polyvinylpyrrolidone (BASF, grade: K30), were dissolved in a solvent (dichloromethane/95% ethanol=6/4) such that the mirabegron concentration became 8 w/v %. This solution was used to obtain a granulated product containing mirabegron, hypromellose, and polyvinylpyrrolidone by using a spray drier (NIHON BUCHI K.K., Mini Spray Dryer B-290). The granulated product of 25.0 g, 65.2 g of polyethylene glycol (NOF CORPORATION, grade: 6000P), and 32.1 g of polyethylene oxide (DOW, grade: N60K) were mixed and screened by using screen No. 22. Wet granulation of the obtained mixed and screened product was performed by using a fluid bed (Flow Coater Mini) with 12.5 g of a solution in which 1.25 g of hydroxypropylcellulose (Nippon Soda Co., Ltd., product name: HPC (SL)) was dissolved. The dried product was sized by screen No. 22. Dibutylhydroxytoluene (Nacalai Tesque Inc.) of 0.2 g and 1.25 g of magnesium stearate (Taihei Chemical Industrial Co., Ltd.) were added to the obtained sized particles. They were mixed in a plastic bag to obtain a powder containing mirabegron before tableting. The powder was then tableted into a tablet having a mass of 250 mg by using a tablet press machine (VELA5, KIKUSUI SEISAKUSHO LTD.), thereby obtaining a mirabegron-containing pharmaceutical preparation according to Example 1. Note that in Example 1, the additive amount ratio PEG/PEO was set to about 67/33.

Example 2

In Example 2, hypromellose and polyvinylpyrrolidone were added by 125% by mass in total with respect to 100% by mass of mirabegron. Note that hypromellose and polyvinylpyrrolidone were added at a ratio of 1:1. Mirabegron of 20.0 g, 12.5 g of hypromellose (Shin-Etsu Chemical Co., Ltd., grade: TC-5E), and 12.5 g of polyvinylpyrrolidone (BASF, grade: K30), were dissolved in a solvent (dichloromethane/95% ethanol=6/4) such that the mirabegron concentration became 8 w/v %. This solution was used to obtain a granulated product containing mirabegron, hypromellose, and polyvinylpyrrolidone by using a spray drier (NIHON BUCHI K.K., Mini Spray Dryer B-290). The granulated product of 22.5 g, 50.47 g of polyethylene glycol, and 24.87 g of polyethylene oxide were mixed and screened by using screen No. 22. Wet granulation of the obtained mixed and screened product was performed by using a fluid bed (Flow Coater Mini) with 10.0 g of solution in which 1.00 g of hydroxypropylcellulose (Nippon Soda Co., Ltd., product name: HPC (SL)) was dissolved. The dried product was sized by screen No. 22. Dibutylhydroxytoluene (Nacalai Tesque Inc.) of 0.16 g and 1.0 g of magnesium stearate (Taihei Chemical Industrial Co., Ltd.) were added to the obtained sized particles. They were mixed in a plastic bag to obtain a powder before tableting. A mirabegron-containing pharmaceutical preparation was then obtained in the same manner as in Example 1 except for the above processes.

Example 3

In Example 3, hypromellose and polyvinylpyrrolidone were added by 150% by mass in total with respect to 100% by mass of mirabegron. Note that hypromellose and polyvinylpyrrolidone were added at a ratio of 1:1. Mirabegron of 20.0 g, 15.0 g of hypromellose (Shin-Etsu Chemical Co., Ltd., grade: TC-5E), and 15.0 g of polyvinylpyrrolidone (BASF, grade: K30), were dissolved in a solvent (dichloromethane/95% ethanol=6/4) such that the mirabegron concentration became 8 w/v %. This solution was used to obtain a granulated product containing mirabegron, hypromellose, and polyvinylpyrrolidone by using a spray drier (NIHON BUCHI K.K., Mini Spray Dryer B-290). The granulated product of 31.25 g, 61.0 g of polyethylene glycol, and 30.05 g of polyethylene oxide were mixed and screened by using screen No. 22. Wet granulation of the obtained mixed and screened product was performed by using a fluid bed (Flow Coater Mini) with 12.5 g of solution in which 1.25 g of hydroxypropylcellulose (Nippon Soda Co., Ltd., product name: HPC (SL)) was dissolved. The dried product was sized by screen No. 22. Dibutylhydroxytoluene (Nacalai Tesque Inc.) of 0.2 g and 1.25 g of magnesium stearate (Taihei Chemical Industrial Co., Ltd.) were added to the obtained sized particles. They were mixed in a plastic bag to obtain a powder before tableting. A mirabegron-containing pharmaceutical preparation was then obtained in the same manner as in Example 1 except for the above processes.

Comparative Example 1

In Comparative Example 1, methylcellulose (MC) was added by 100% by mass with respect to 100% by mass of mirabegron. Mirabegron of 20.0 g and 20.0 g of methyl lose (Shin-Etsu Chemical Co., Ltd., grade: SM4) were dissolved in a solvent (dichloromethane/95% ethanol=6/4) such that the mirabegron concentration became 8 w/v %. This solution was used to obtain a granulated product containing mirabegron and methylcellulose by using a spray drier (NIHON BUCHI K.K., Mini Spray Dryer B-290). The granulated product of 25.0 g, 65.2 g of polyethylene glycol, and 32.1 g of polyethylene oxide were mixed and screened by using screen No. 22. Wet granulation of the obtained mixed and screened product was performed by using a fluid bed (Flow Coater Mini) with 12.5 g of solution in which 1.25 g of hydroxypropylcellulose (Nippon Soda Co., Ltd., product name: HPC (SL)) was dissolved. The dried product was sized by screen No. 22. Dibutylhydroxytoluene (Nacalai Tesque Inc.) of 0.2 g and 1.25 g of magnesium stearate (Taihei Chemical Industrial Co., Ltd.) were added to the obtained sized particles. They were mixed in a plastic bag to obtain a powder before tableting. A mirabegron-containing pharmaceutical preparation was then obtained in the same manner as in Example 1 except for the above processes.

Comparative Example 2

In Comparative Example 2, hypromellose was added by 50% by mass with respect to 100% by mass of mirabegron. Mirabegron of 20.0 g and 10.0 g of hypromellose (Shin-Etsu Chemical Co., Ltd., grade: TC-5E) were dissolved in a solvent (dichloromethane/95% ethanol=6/4) such that the mirabegron concentration became 8 w/v %. This solution was used to obtain a granulated product containing mirabegron and hypromellose by using a spray drier (NIHON BUCHI K.K., Mini Spray Dryer B-290). The granulated product of 9.0 g, 33.6 g of polyethylene glycol, and 16.1 g of polyethylene oxide were mixed and screened by using screen No. 22. Wet granulation of the obtained mixed and screened product was performed by using a fluid bed (Flow Coater Mini) with 6.0 g of solution in which 0.6 g of hydroxypropylcellulose (Nippon Soda Co., Ltd., product name: HPC (SL)) was dissolved. The dried product was sized by screen No. 22. Dibutylhydroxytoluene (Nacalai Tesque Inc.) of 0.1 g and 0.6 g of magnesium stearate (Taihei Chemical Industrial Co., Ltd.) were added to the obtained sized particles. They were mixed in a plastic bag to obtain a powder before tableting. A mirabegron-containing pharmaceutical preparation was then obtained in the same manner as in Example 1 except for the above processes.

Comparative Example 3

In Comparative Example 3, hypromellose was added by 100% by mass with respect to 100% by mass of mirabegron. Mirabegron of 20.0 g and 20.0 g of hypromellose (manufacturer: Shin-Etsu Chemical Co., Ltd., grade: TC-5E) were dissolved in a solvent (dichloromethane/95% ethanol=6/4) such that the mirabegron concentration became 8 w/v %. This solution was used to obtain a granulated product containing mirabegron and hypromellose by using a spray drier (NIHON BUCHI K.K., Mini Spray Dryer B-290). The granulated product of 10.0 g, 27.0 g of polyethylene glycol, and 11.92 g of polyethylene oxide were mixed and screened by using screen No. 22. Wet granulation of the obtained mixed and screened product was performed by using a fluid bed (Flow Coater Mini) with 5.0 g of solution in which 0.5 g of hydroxypropylcellulose (Nippon Soda Co., Ltd., product name: HPC (SL)) was dissolved. The dried product was sized by screen No. 22. Dibutylhydroxytoluene (Nacalai Tesque Inc.) of 0.08 g and 0.5 g of magnesium stearate (Taihei Chemical Industrial Co., Ltd.) were added to the obtained sized particles. They were mixed in a plastic bag to obtain a powder before tableting. A mirabegron-containing pharmaceutical preparation was then obtained in the same manner as in Example 1 except for the above processes.

Comparative Example 4

In Comparative Example 4, hypromellose was added by 125% by mass with respect to 100% by mass of mirabegron. Mirabegron of 20.0 g and 25.0 g of hypromellose (Shin-Etsu Chemical Co., Ltd., grade: TC-5E) were dissolved in a solvent (dichloromethane/95% ethanol=6/4) such that the mirabegron concentration became 8 w/v %. This solution was used to obtain a granulated product containing mirabegron and hypromellose by using a spray drier (NIHON BUCHI K.K., Mini Spray Dryer B-290). The granulated product of 22.5 g, 50.47 g of polyethylene glycol, and 24.87 g of polyethylene oxide were mixed and screened by using screen No. 22. Wet granulation of the obtained mixed and screened product was performed by using a fluid bed (Flow Coater Mini) with 10.0 g of solution in which 1.0 g of hydroxypropylcellulose (Nippon Soda Co., Ltd., product name: HPC (SL)) was dissolved. The dried product was sized by screen No. 22. Dibutylhydroxytoluene (Nacalai Tesque Inc.) of 0.16 g and 1.0 g of magnesium stearate (Taihei Chemical Industrial Co., Ltd.) were added to the obtained sized particles. They were mixed in a plastic bag to obtain a powder before tableting. A mirabegron-containing pharmaceutical preparation was then obtained in the same manner as in Example 1 except for the above processes.

Comparative Example 5

In Comparative Example 5, hypromellose was added by 150% by mass with respect to 100% by mass of mirabegron. Mirabegron of 20.0 g and 30.0 g of hypromellose (Shin-Etsu Chemical Co., Ltd., grade: TC-5E) were dissolved in a solvent (dichloromethane/95% ethanol=6/4) such that the mirabegron concentration became 8 w/v %. This solution was used to obtain a granulated product containing mirabegron and hypromellose by using a spray drier (NIHON BUCHI K.K., Mini Spray Dryer B-290). The granulated product of 31.25 g, 61.0 g of polyethylene glycol, and 30.05 g of polyethylene oxide were mixed and screened by using screen No. 22. Wet granulation of the obtained mixed and screened product was performed by using a fluid bed (Flow Coater Mini) with 12.5 g of solution in which 1.25 g of hydroxypropylcellulose (Nippon Soda Co., Ltd., product name: HPC (SL)) was dissolved. The dried product was sized by screen No. 22. Dibutylhydroxytoluene (Nacalai Tesque Inc.) of 0.20 g and 1.25 g of magnesium stearate (Taihei Chemical Industrial Co., Ltd.) were added to the obtained sized particles. They were mixed in a plastic bag to obtain a powder before tableting. A mirabegron-containing pharmaceutical preparation was then obtained in the same manner as in Example 1 except for the above processes.

Comparative Example 6

In Comparative Example 6, polyvinylpyrrolidone was added by 50% by mass with respect to 100% by mass of mirabegron. Mirabegron of 20.0 g and 10.0 g of polyvinylpyrrolidone (BASF, grade: K30) were dissolved in a solvent (dichloromethane/95% ethanol=6/4) such that the mirabegron concentration became 8 w/v %. This solution was used to obtain a granulated product containing mirabegron and polyvinylpyrrolidone by using a spray drier (NIHON BUCHI K.K., Mini Spray Dryer B-290). The granulated product of 15.0 g, 56.0 g of polyethylene glycol, and 26.84 g of polyethylene oxide were mixed and screened by using screen No. 22. Wet granulation of the obtained mixed and screened product was performed by using a fluid bed (Flow Coater Mini) with 10.0 g of solution in which 1.0 g of hydroxypropylcellulose (Nippon Soda Co., Ltd., product name: HPC (SL)) was dissolved. The dried product was sized by screen No. 22. Dibutylhydroxytoluene (Nacalai Tesque Inc.) of 0.16 g and 1.0 g of magnesium stearate (Taihei Chemical Industrial Co., Ltd.) were added to the obtained sized particles. They were mixed in a plastic bag to obtain a powder before tableting. A mirabegron-containing pharmaceutical preparation was then obtained in the same manner as in Example 1 except for the above processes.

Comparative Example 7

In Comparative Example 7, polyvinylpyrrolidone was added by 100% by mass with respect to 100% by mass of mirabegron. Mirabegron of 20.0 g and 20.0 g of polyvinylpyrrolidone (BASF, grade: K30) were dissolved in a solvent (dichloromethane/95% ethanol=6/4) such that the mirabegron concentration became 8 w/v %. This solution was used to obtain a granulated product containing mirabegron and polyvinylpyrrolidone by using a spray drier (NIHON BUCHI K.K., Mini Spray Dryer B-290). The granulated product of 20.0 g, 54.0 g of polyethylene glycol, and 23.84 g of polyethylene oxide were mixed and screened by using screen No. 22. Wet granulation of the obtained mixed and screened product was performed by using a fluid bed (Flow Coater Mini) with 10.0 g of solution in which 1.0 g of hydroxypropylcellulose (Nippon Soda Co., Ltd., product name: HPC (SL)) was dissolved. The dried product was sized by screen No. 22. Dibutylhydroxytoluene (Nacalai Tesque Inc.) of 0.16 g and 1.0 g of magnesium stearate (Taihei Chemical Industrial Co., Ltd.) were added to the obtained sized particles. They were mixed in a plastic bag to obtain a powder before tableting. A mirabegron-containing pharmaceutical preparation was then obtained in the same manner as in Example 1 except for the above processes.

Comparative Example 8

In Comparative Example 8, polyvinylpyrrolidone was added by 125% by mass with respect to 100% by mass of mirabegron. Mirabegron of 40.0 g and 50.0 g of polyvinylpyrrolidone (BASF, grade: K30) were dissolved in a solvent (dichloromethane/95% ethanol=6/4) such that the mirabegron concentration became 8 w/v %. This solution was used to obtain a granulated product containing mirabegron and polyvinylpyrrolidone by using a spray drier (NIHON BUCHI K.K., Mini Spray Dryer B-290). The granulated product of 28.13 g, 63.09 g of polyethylene glycol, and 31.09 g of polyethylene oxide were mixed and screened by using screen No. 22. Wet granulation of the obtained mixed and screened product was performed by using a fluid bed (Flow Coater Mini) with 12.5 g of solution in which 1.25 g of hydroxypropylcellulose (Nippon Soda Co., Ltd., product name: HPC (SL)) was dissolved. The dried product was sized by screen No. 22. Dibutylhydroxytoluene (Nacalai Tesque Inc.) of 0.20 g and 1.25 g of magnesium stearate (Taihei Chemical Industrial Co., Ltd.) were added to the obtained sized particles. They were mixed in a plastic bag to obtain a powder before tableting. A mirabegron-containing pharmaceutical preparation was then obtained in the same manner as in Example 1 except for the above processes.

Comparative Example 9

In Comparative Example 9, polyvinylpyrrolidone was added by 150% by mass with respect to 100% by mass of mirabegron. Mirabegron of 20.0 g and 30.0 g of polyvinylpyrrolidone (BASF, grade: K30) were dissolved in a solvent (dichloromethane/95% ethanol=6/4) such that the mirabegron concentration became 8 w/v %. This solution was used to obtain a granulated product containing mirabegron and polyvinylpyrrolidone by using a spray drier (NIHON BUCHI K.K., Mini Spray Dryer B-290). The granulated product of 31.25 g, 61.0 g of polyethylene glycol, and 30.05 g of polyethylene oxide were mixed and screened by using screen No. 22. Wet granulation of the obtained mixed and screened product was performed by using a fluid bed (Flow Coater Mini) with 12.5 g of solution in which 1.25 g of hydroxypropylcellulose (Nippon Soda Co., Ltd., product name: HPC (SL)) was dissolved. The dried product was sized by screen No. 22. Dibutylhydroxytoluene (Nacalai Tesque Inc.) of 0.20 g and 1.25 g of magnesium stearate (Taihei Chemical Industrial Co., Ltd.) were added to the obtained sized particles. They were mixed in a plastic bag to obtain a powder before tableting. A mirabegron-containing pharmaceutical preparation was then obtained in the same manner as in Example 1 except for the above processes.

(Verification of Amorphization)

Verifications have been made on the mirabegron-containing pharmaceutical preparations according to Examples 1 to 3 and Comparative Examples 1 to 9 by a powder X-ray diffraction (PXRD) apparatus (D8 ADVANCE available from Bruker AXS K.K.) using Cuk$\alpha$ to check whether amorphous form can be maintained. First of all, the pharmaceutical preparations according to Examples 1 to 3 and Comparative Examples 1 to 9 stored in aluminum bags under the conditions of a temperature of 40° C. and a humidity of 75 RH % were ground by using agate mortar. The ground pharmaceutical preparations were then packed in PXRD measurement sample cups. Each pharmaceutical preparation was set in the PXRD apparatus. The tube voltage and the tube current were respectively set to 40 kV and 40 mV, and scanning was performed in the range of scanning axis 2θ from 2° to 40° with a measurement step width of 0.015° at a rate of measurement time 0.1 sec/step.

Figure 1:
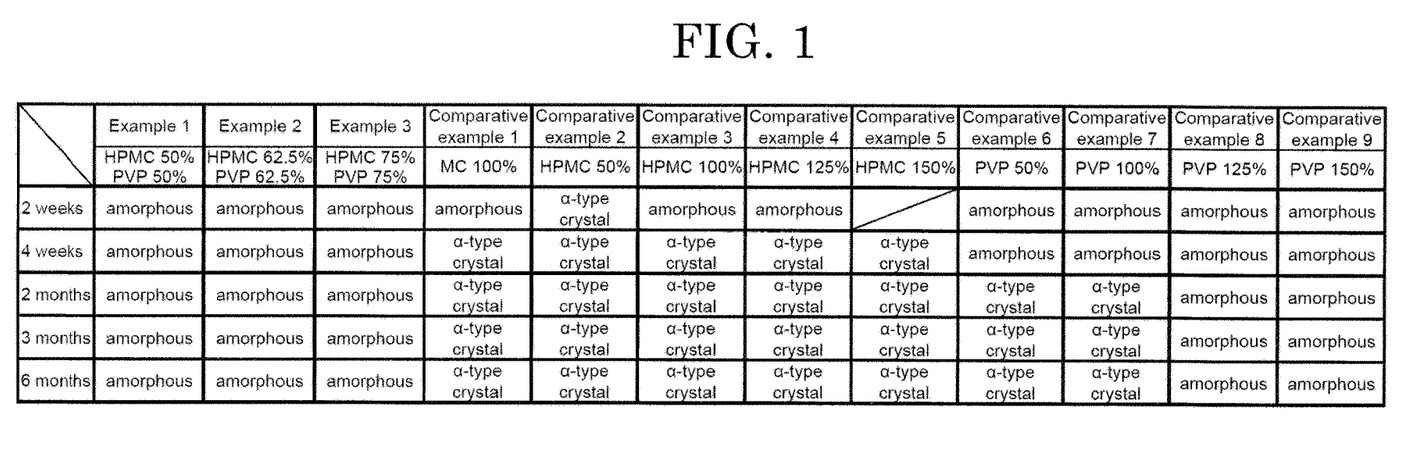
FIG. 1 is a view showing the crystal forms of mirabegron in pharmaceutical preparations containing the granulated products obtained from mirabegron and various types of polymers according to an example of the present invention.

FIG. 1 shows verification results. In each of the mirabegron-containing pharmaceutical preparations according to Examples 1 to 3, which contained 100% or more by mass of hypromellose and polyvinylpyrrolidone in total with respect to the 100% by mass of mirabegron, it was found that the amorphous form of the mirabegron was maintained even after 6-month storage. In addition, in each of Comparative Examples 6 to 9 added only polyvinylpyrrolidone, it was found that addition of 125% or more by mass of polyvinylpyrrolidone maintained the amorphous form of mirabegron even after 6-month storage. In contrast to this, in Comparative Example 1 added methylcellulose, crystal transformation to the α-type occurred after about 1 month of storage. In each of Comparative Examples 2 to 5 added only hypromellose, crystal transformation to the α-type was confirmed after at least about 1-month storage.

(Related Substances)

The stability of each of the mirabegron-containing pharmaceutical preparations according to Examples 1 to 3 and Comparative Examples 1 to 9 was evaluated by evaluating the purity of the mirabegron in each of the pharmaceutical preparations according to Examples 1 to 3 and Comparative Examples 1 to 9 which was stored in an aluminum bag under the conditions of a temperature of 40° C. and a humidity of 75 RH % by using a liquid chromatography. Total of related substances was obtained by calculating each ratio of the related substances corresponding to each peak area of the related substances originating from mirabegron.

Figure 2:
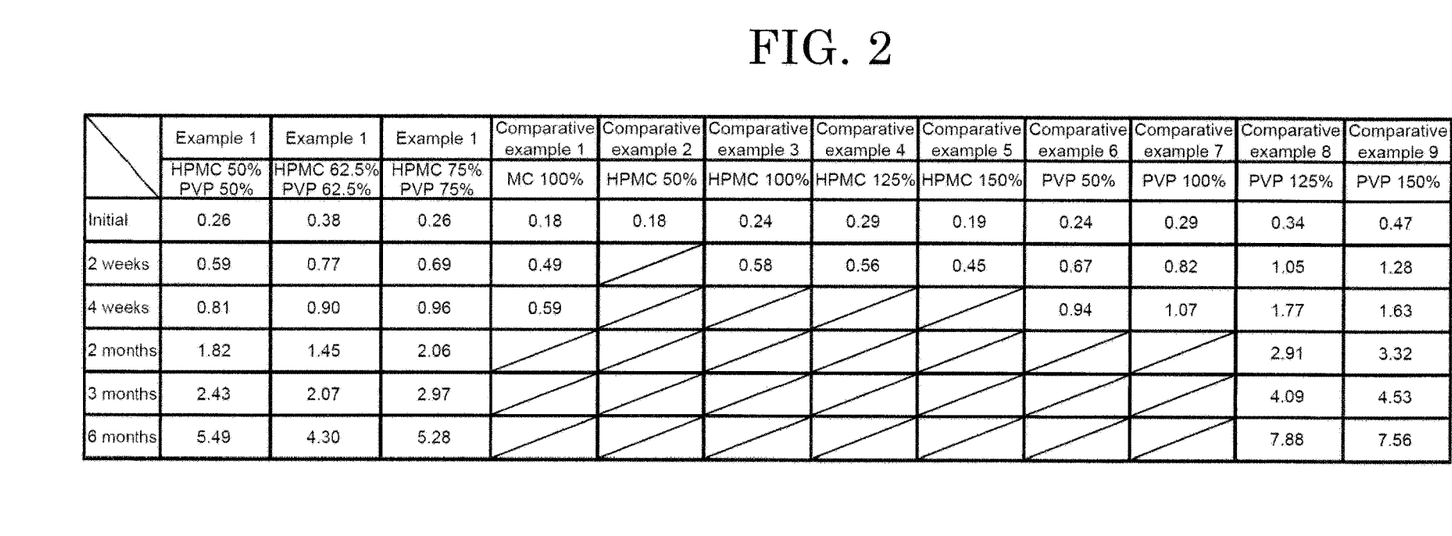
FIG. 2 is a view showing the total related substance amounts of pharmaceutical preparations containing the granulated products obtained from mirabegron and various types of polymers according to an example of the present invention.

FIG. 2 shows measurement results on the related substances in Examples 1 to 3 and Comparative Examples 1 to 9. In each of Comparative Examples 6 to 9 added only polyvinylpyrrolidone, although the amorphous form was maintained, it was found that related substances noticeably increased during long-term storage. In contrast to this, in Comparative Examples 2 to 5 added only hypromellose, it was found that increases in related substances can be reduced more than in Comparative Examples 6 to 9 added only polyvinylpyrrolidone. It was thought that this was because the amorphous form of the mirabegron was transformed to the α-crystal form due to long-term storage. In contrast to this, in the mirabegron-containing pharmaceutical preparations according to Examples 1 to 3, it was found that the amorphous form of the mirabegron was maintained even after 6-month storage and increases in related substances after long-term storage were significantly reduced as compared with Comparative Examples 6 to 9 added only polyvinylpyrrolidone.

It is revealed that hypromellose prevents the generation of related substances of the mirabegron although the effect of maintaining the amorphous form of the mirabegron is low. It is also revealed that polyvinylpyrrolidone generates related substances of the mirabegron although the effect of maintaining the amorphous form of the mirabegron is high. The above test results have revealed that hypromellose and polyvinylpyrrolidone exhibit complementary actions in the mirabegron-containing pharmaceutical preparation. The above effect obtained by using both such hypromellose and polyvinylpyrrolidone with respect to the mirabegron-containing pharmaceutical preparation has not been reported so far. This is a totally new finding.

Example 4

In Example 4, studies have been made to determine whether the additive amounts of polyethylene glycol and polyethylene oxide as sustained-release additives influence the dissolution performance of mirabegron. In Example 4, hypromellose and polyvinylpyrrolidone were added by 150% by mass in total with respect to 100% by mass of mirabegron. Note that hypromellose and polyvinylpyrrolidone were added at a ratio of 1:1. Mirabegron of 100.0 g, 75.0 g of hypromellose (Shin-Etsu Chemical Co., Ltd., grade: TC-5E), and 75.0 g of polyvinylpyrrolidone (BASF, grade: K30), were dissolved in a solvent (dichloromethane/95% ethanol=6/4) such that the mirabegron concentration became 8 w/v %. This solution was used to obtain a granulated product containing mirabegron, hypromellose, and polyvinylpyrrolidone by using a spray drier (NIHON BUCHI K.K., Mini Spray Dryer B-290). The granulated product of 150.0 g, 93.6 g of polyethylene glycol (NOF CORPORATION, grade: 6000P), and 46.92 g of polyethylene oxide (DOW, grade: N60K) were mixed and screened by using screen No. 22. Wet granulation of the obtained mixed and screened product was performed by using a fluid bed (MP-01) with 120.0 g of a solution in which 6.0 g of hypromellose (Shin-Etsu Chemical Co., Ltd., grade: TC-5R) was dissolved. The dried product was sized by screen No. 22. Dibutylhydroxytoluene (Nacalai Tesque Inc.) of 0.48 g and 3.0 g of magnesium stearate (Taihei Chemical Industrial Co., Ltd.) were added to the obtained sized particles. They were mixed in a plastic bag to obtain a powder containing mirabegron before tableting. The powder before tableting was then tableted into a tablet having a mass of 250 mg by using a tablet press machine (VELA5, KIKUSUI SEISAKUSHO LTD.), thereby obtaining a mirabegron-containing pharmaceutical preparation according to Example 4. Note that the content of mirabegron per tablet of the mirabegron-containing pharmaceutical preparation according to Example 4 is 50 mg.

Example 5

In Example 5, the additive amount ratio (HPMC+PVP+PEG)/PEO was set to 73/27. A mirabegron-containing pharmaceutical preparation was obtained in the same manner as in Example 4 except that 79.2 g of polyethylene glycol and 61.32 g of polyethylene oxide were added to obtain powder before tableting.

Example 6

In Example 6, the additive amount ratio (HPMC+PVP+PEG)/PEO was set to 67/33. A mirabegron-containing pharmaceutical preparation was obtained in the same manner as in Example 4 except that 64.44 g of polyethylene glycol and 76.08 g of polyethylene oxide were added to obtain powder before tableting.
(Verification of Amorphization)

Figure 3:
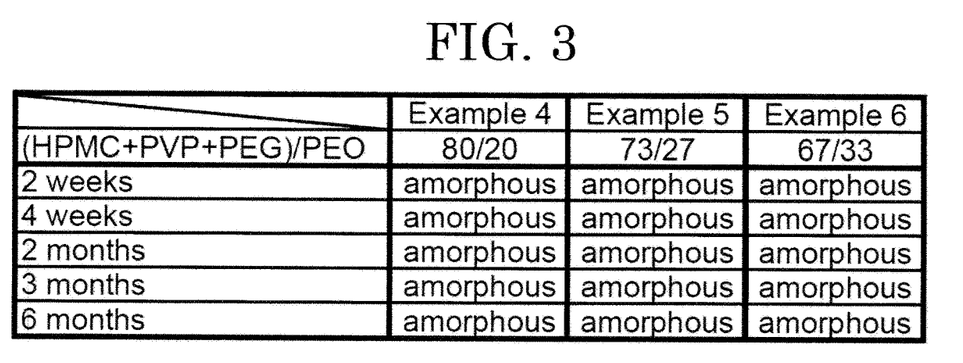
FIG. 3 is a view showing the crystal forms of mirabegron in pharmaceutical preparations containing the granulated products obtained from mirabegron and various types of polymers according to an example of the present invention.

Verifications have been made on the mirabegron-containing pharmaceutical preparations according to Examples 4 to 6 to check whether amorphous form can be maintained. X-ray diffractions were obtained from the pharmaceutical preparations according to Examples 4 to 6, each of which was stored in an aluminum bag under the conditions of a temperature of 40° C. and a humidity of 75 RH %. Because the same X-ray diffraction experimental method as that described above was used, a detailed description of the method will be omitted. FIG. 3 shows test results. In the mirabegron-containing pharmaceutical preparation according to each example, it was found that the amorphous of the mirabegron was maintained even after 6-month storage.
(Dissolution Tests)

Figure 4:
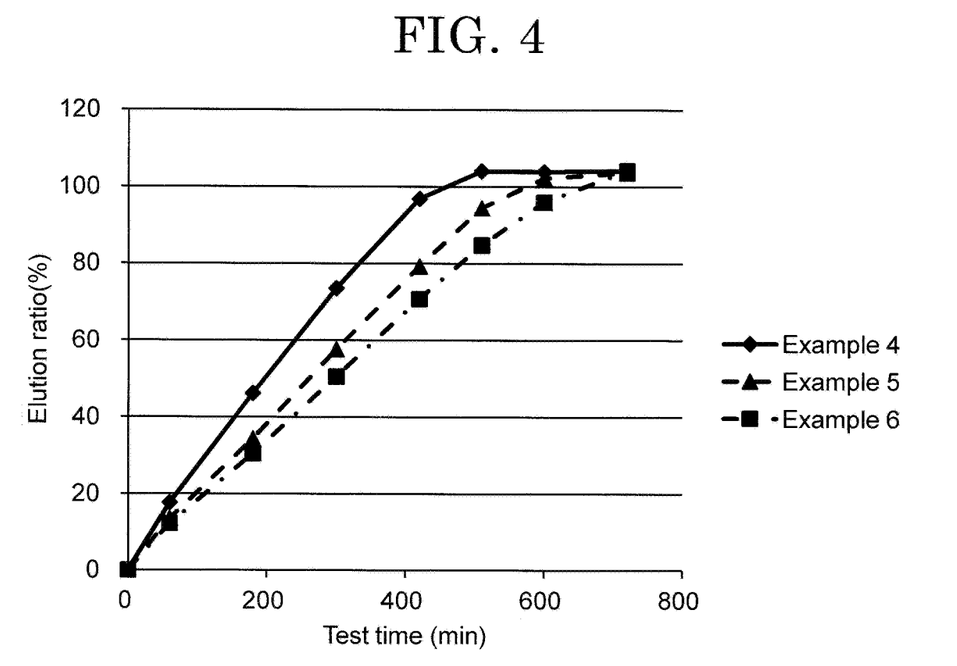
FIG. 4 is a graph showing the dissolution behaviors of mirabegron pharmaceutical preparations depending on the compounding ratio between polyethylene glycol and polyethylene oxide according to an example of the present invention (basket method: USP pH 6.8 buffer solution, 900 mL, 100 rpm)

A pH 6.8 USP buffer of 900 ml was used as a test solution, and each of the mirabegron-containing pharmaceutical preparations according to Examples 4 to 6 was agitated for 0 min, 60 mins, 180 mins, 300 mins, 420 mins, 510 mins, 600 mins, and 720 mins in conformity with USP Apparatus 1 (rotating basket method) to measure dissolution rates in the respective form. FIG. 4 shows the measurement results obtained by the dissolution tests. The results shown in FIG. 4 revealed that the dissolution behavior of mirabegron was able to be controlled by adjusting the additive amount ratio (HPMC+PVP+PEG)/PEO.

Example 7

In Example 7, studies have been made to determine whether the grade of polyethylene glycol as a sustained-release additive influences the dissolution performance of mirabegron. In Example 7, PEG8000PF $D_{50}$=52 μm was used. Hypromellose and polyvinylpyrrolidone were added by 150% by mass in total with respect to 100% by mass of mirabegron. Note that hypromellose and polyvinylpyrrolidone were added at a ratio of 1:1. Mirabegron of 100.0 g, 75.0 g of hypromellose (Shin-Etsu Chemical Co., Ltd., grade: TC-5E), and 75.0 g of polyvinylpyrrolidone (BASF, grade: K30), were dissolved in a solvent (dichloromethane/95% ethanol=6/4) such that the mirabegron concentration became 8 w/v %. This solution was used to obtain a granulated product containing mirabegron, hypromellose, and polyvinylpyrrolidone by using a spray drier (NIHON BUCHI K.K., Mini Spray Dryer B-290). The granulated product of 75.0 g, 144 g of polyethylene glycol (DOW, grade: 8000PF), and 71.52 g of polyethylene oxide (DOW, grade: N60K) were mixed and screened by using screen No. 22. Wet granulation of the obtained mixed and screened product was performed by using a fluid bed (MP-01) with 120.0 g of a solution in which 6.0 g of hypromellose (Shin-Etsu Chemical Co., Ltd., grade: TC-5R) was dissolved. The dried product was sized by screen No. 22. Dibutylhydroxytoluene (Nacalai Tesque Inc.) of 0.48 g and 3.0 g of magnesium stearate (Taihei Chemical Industrial Co., Ltd.) were added to the obtained sized particles. They were mixed in a plastic bag to obtain a powder containing mirabegron before tableting. The powder was then tableted into a tablet having a mass of 250 mg by using a tablet press machine (VELA5, KIKUSUI SEISAKUSHO LTD.), thereby obtaining a mirabegron-containing pharmaceutical preparation according to Example 7. Note that the content of mirabegron per tablet of the mirabegron-containing pharmaceutical preparation according to Example 7 is 25 mg.

Example 8

In Example 8, a mirabegron-containing pharmaceutical preparation was obtained in the same manner as in Example 7 except that PEG6000 (NOF CORPORATION) $D_{50}$=94 μm was used.

Example 9

In Example 9, a mirabegron-containing pharmaceutical preparation was obtained in the same manner as in Example 7 except that PEG8000P (Clariant) $D_{50}$=211 μm was used.
(Dissolution Tests)

Figure 5:
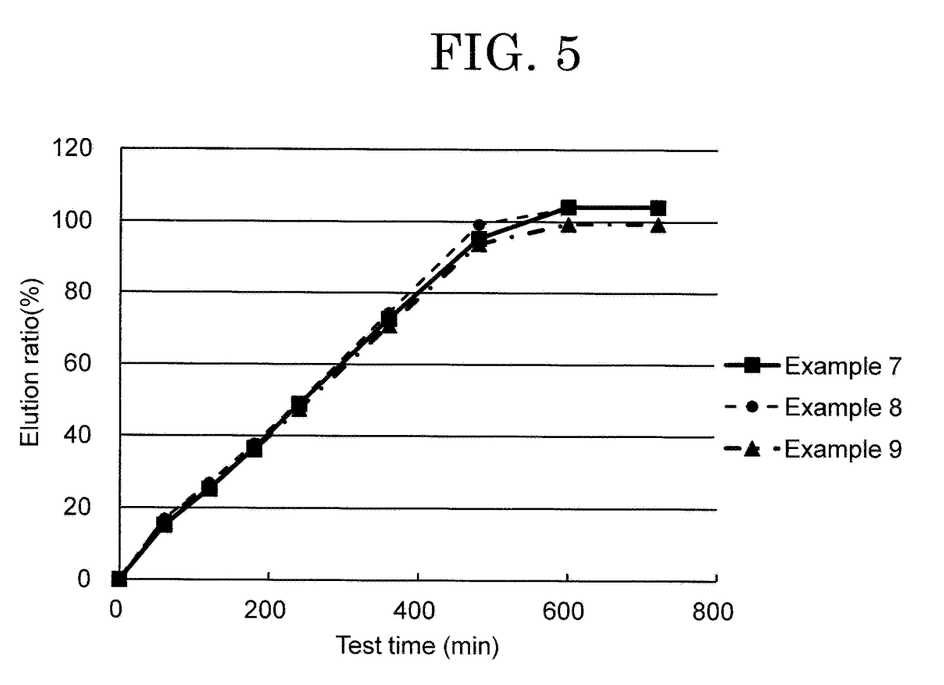
FIG. 5 is a graph showing the dissolution behaviors of mirabegron pharmaceutical preparations depending on the grade of polyethylene glycol according to an example of the present invention (basket method: USP pH 6.8 buffer solution, 900 mL, 100 rpm).

A pH 6.8 USP buffer of 900 ml was used as a test solution, and each of the mirabegron-containing pharmaceutical preparations according to Examples 7 to 9 was agitated for 0 min, 60 mins, 120 mins, 180 mins, 240 mins, 360 mins, 480 mins, 600 mins, and 720 mins in conformity with USP Apparatus 1 (rotating basket method) to measure dissolution rates in the respective form. FIG. 5 shows the measurement results obtained by the dissolution tests. The results shown in FIG. 5 revealed that the grade of polyethylene glycol did not influence the dissolution behavior of mirabegron.

The present invention provides a mirabegron-containing tablet that maintains the amorphous form of mirabegron even after long-term storage. The present invention also provides a mirabegron-containing pharmaceutical preparation that can maintain the purity of mirabegron while preventing the generation of related substances at the time of storage, a method for producing a mirabegron-containing pharmaceutical preparation, and a method for producing a mirabegron-containing granulated product.

What is claimed is:
1. A method for producing a mirabegron-containing pharmaceutical preparation, comprising:
    dissolving mirabegron, hypromellose, and polyvinylpyrrolidone in a solvent, wherein the solvent comprises dichloromethane and ethanol;
    spray-drying and granulating a solution containing the mirabegron, the hypromellose, and the polyvinylpyrrolidone by using a spray drier;
    performing wet granulation of the obtained spray-dried granulated product with a pharmaceutically acceptable additive, wherein the pharmaceutically acceptable additive comprises polyethylene oxide (PEO) or polyethylene glycol (PEG); and
    tableting a mixed powder containing the obtained granulated particles.
2. The method for producing a mirabegron-containing pharmaceutical preparation according to claim 1, wherein the solution contains 100% or more by mass of the hypromellose and the polyvinylpyrrolidone in total with respect to a content of the mirabegron.

3. A method for producing a mirabegron-containing granulated product, comprising:
- dissolving mirabegron, hypromellose, and polyvinylpyrrolidone in a solvent, wherein the solvent comprises dichloromethane and ethanol;
- spray-drying and granulating a solution containing the mirabegron, the hypromellose, and the polyvinylpyrrolidone by using a spray drier; and
- performing wet granulation of the obtained spray-dried granulated product with a pharmaceutically acceptable additive, wherein the pharmaceutically acceptable additive comprises polyethylene oxide (PEO) or polyethylene glycol (PEG).

4. The method for producing a mirabegron-containing granulated product according to claim 3, wherein the solution contains 100% or more by mass of the hypromellose and the polyvinylpyrrolidone in total with respect to a content of the mirabegron.

5. The method according to claim 1, wherein the pharmaceutically acceptable additive comprises polyethylene oxide (PEO) and polyethylene glycol (PEG).

6. The method according to claim 3, wherein the pharmaceutically acceptable additive comprises polyethylene oxide (PEO) and polyethylene glycol (PEG).

* * * * *